(12) United States Patent
Ruppersberg (10) Patent No.: US 9,526,810 B2
(45) Date of Patent: Dec. 27, 2016

(54) SYSTEMS, DEVICES, COMPONENTS AND METHODS FOR IMPROVED ACOUSTIC COUPLING BETWEEN A BONE CONDUCTION HEARING DEVICE AND A PATIENT'S HEAD OR SKULL

(71) Applicant: Sophono, Inc., Boulder, CO (US)

(72) Inventor: Peter Ruppersberg, Blonay (CH)

(73) Assignee: SOPHONO, INC., Boulder, CO (US)

( * ) Notice: Subject to any disclaimer, the term of this patent is extended or adjusted under 35 U.S.C. 154(b) by 0 days.

(21) Appl. No.: 14/516,392

(22) Filed: Oct. 16, 2014

(65) Prior Publication Data

US 2015/0038775 A1  Feb. 5, 2015

Related U.S. Application Data

(63) Continuation-in-part of application No. 13/550,581, filed on Jul. 16, 2012, and a continuation-in-part of
(Continued)

(51) Int. Cl.
*A61L 24/06* (2006.01)
*A61L 24/00* (2006.01)
(Continued)

(52) U.S. Cl.
CPC .......... *A61L 24/06* (2013.01); *A61L 24/0031* (2013.01); *H04R 25/606* (2013.01); *H04R 3/002* (2013.01);
(Continued)

(58) Field of Classification Search
None
See application file for complete search history.

(56) References Cited

U.S. PATENT DOCUMENTS 4,352,960 A  10/1982  Dormer et al.
4,612,915 A   9/1986  Hough et al.
(Continued)

FOREIGN PATENT DOCUMENTS

WO  WO 2007024657 A2 *  3/2007  ............ H04R 25/00
WO  2010/105601  9/2010
(Continued)

OTHER PUBLICATIONS

Vengerova et al "Medical Gels for Ultrasonic Diagnosis, Therapy, and Electrocardiography." p. 57-58. Jan.-Feb. 1994.*
(Continued)

*Primary Examiner* — Curtis Kuntz
*Assistant Examiner* — Qin Zhu
(74) *Attorney, Agent, or Firm* — Jeffrey J. Hohenshell (57) ABSTRACT

Disclosed are various embodiments of systems, devices, components and methods for improving acoustic coupling between a bone conduction hearing device (BCHD) and a patient's head or skull. Such systems, devices, components and methods include disposing a gel or paste between the BCHD and the patient's skin, hair and/or skull. The gel or paste improves the transmission of acoustic signals generated by a transducer in the BCHD to the patients head or skull by providing a more efficient and improved intermediary acoustic medium for the transmission of acoustic signals to the patient's head or skull.

37 Claims, 10 Drawing Sheets

Related U.S. Application Data application No. 13/650,026, filed on Oct. 11, 2012, and a continuation-in-part of application No. 13/650,057, filed on Oct. 11, 2012, and a continuation-in-part of application No. 13/650,080, filed on Oct. 11, 2012, and a continuation-in-part of application No. 13/649,934, filed on Oct. 11, 2012, and a continuation-in-part of application No. 13/256,571, filed on Dec. 9, 2011, and a continuation-in-part of application No. 13/804,420, filed on Mar. 14, 2013, and a continuation-in-part of application No. 13/793,218, filed on Mar. 11, 2013, and a continuation-in-part of application No. 14/288,181, filed on May 27, 2014, and a continuation-in-part of application No. 14/288,142, filed on May 27, 2014.

(60) Provisional application No. 61/970,336, filed on Mar. 25, 2014.

(51) Int. Cl.
    *H04R 25/00*    (2006.01)
    *H04R 3/00*    (2006.01)

(52) U.S. Cl.
    CPC ....... *H04R 2225/67* (2013.01); *H04R 2460/13* (2013.01)

(56) References Cited

U.S. PATENT DOCUMENTS

| | | | |
|---|---|---|---|
| 4,726,378 A | 2/1988 | Kaplan | |
| 4,736,747 A | 4/1988 | Drake | |
| RE32,947 E | 6/1989 | Dormer | |
| 4,918,745 A | 4/1990 | Hutchinson | |
| 4,918,757 A * | 4/1990 | Janssen | H04R 25/02 2/171 |
| 5,558,618 A | 9/1996 | Maniglia | |
| 5,906,635 A | 5/1999 | Maniglia | |
| 6,039,694 A * | 3/2000 | Larson | A61B 8/4281 600/459 |
| 6,246,911 B1 | 6/2001 | Seligman | |
| 6,358,281 B1 | 3/2002 | Berrang et al. | |
| 6,517,476 B1 | 2/2003 | Bedoya et al. | |
| 6,537,200 B2 | 3/2003 | Leysieffer | |
| 6,565,503 B2 | 5/2003 | Leysieffer | |
| 6,631,197 B1 * | 10/2003 | Taenzer | H04R 25/606 381/312 |
| 6,648,914 B2 | 11/2003 | Berrang et al. | |
| 7,186,211 B2 | 3/2007 | Schneider et al. | |
| 7,386,143 B2 | 6/2008 | Easter et al. | |
| 7,599,508 B1 | 10/2009 | Lynch | |
| 7,856,986 B2 | 12/2010 | Darley | |
| 8,107,661 B1 | 1/2012 | Lynch | |
| 8,170,253 B1 | 5/2012 | Lynch | |
| 8,255,058 B2 | 8/2012 | Gibson et al. | |
| 8,270,647 B2 | 9/2012 | Crawford et al. | |
| 8,315,705 B2 | 11/2012 | Keuninckx | |
| 8,369,959 B2 | 2/2013 | Meskens | |
| 8,406,443 B2 | 3/2013 | Westerkull et al. | |
| 8,452,412 B2 | 5/2013 | Ibrahim | |
| 8,515,112 B2 | 8/2013 | Crawford et al. | |
| 8,538,545 B2 | 9/2013 | Meskens | |
| 8,771,204 B2 * | 7/2014 | Telfort et al. | 600/586 |
| 8,774,930 B2 | 7/2014 | Ball | |
| 8,787,608 B2 | 7/2014 | Van Himbeeck et al. | |
| 8,811,643 B2 | 8/2014 | Crawford et al. | |
| 8,891,795 B2 | 11/2014 | Andersson | |
| 8,897,475 B2 | 11/2014 | Ball | |
| 8,897,883 B2 | 11/2014 | Griffith | |
| 8,923,968 B2 | 12/2014 | Meskens | |
| 8,934,984 B2 | 1/2015 | Meskens et al. | |
| 9,020,174 B2 | 4/2015 | Asnes | |
| 2004/0202339 A1 * | 10/2004 | O'Brien, Jr. | H04B 13/005 381/312 |
| 2005/0038368 A1 * | 2/2005 | Richter et al. | 602/41 |
| 2007/0053536 A1 | 3/2007 | Westerkull | |
| 2007/0274551 A1 * | 11/2007 | Tsai et al. | 381/326 |
| 2007/0286440 A1 * | 12/2007 | Abolfathi et al. | 381/312 |
| 2009/0248155 A1 | 10/2009 | Parker | |
| 2009/0299437 A1 | 12/2009 | Zimmerling | |
| 2010/0145135 A1 | 6/2010 | Ball et al. | |
| 2010/0179375 A1 * | 7/2010 | Andersson et al. | 600/25 |
| 2011/0022120 A1 | 1/2011 | Ball et al. | |
| 2011/0216927 A1 | 9/2011 | Ball | |
| 2011/0257571 A1 * | 10/2011 | Fritsch et al. | 602/46 |
| 2012/0029267 A1 | 2/2012 | Ball | |
| 2012/0041515 A1 | 2/2012 | Meskens et al. | |
| 2012/0078035 A1 | 3/2012 | Andersson et al. | |
| 2012/0080039 A1 | 4/2012 | Siegert | |
| 2012/0088957 A1 | 4/2012 | Adamson et al. | |
| 2012/0238799 A1 | 9/2012 | Ball et al. | |
| 2012/0294466 A1 * | 11/2012 | Kristo et al. | 381/322 |
| 2012/0296155 A1 | 11/2012 | Ball | |
| 2012/0302823 A1 | 11/2012 | Andersson | |
| 2013/0018218 A1 | 1/2013 | Haller et al. | |
| 2013/0046131 A1 | 2/2013 | Ball et al. | |
| 2013/0089229 A1 * | 4/2013 | Kristo et al. | 381/326 |
| 2013/0150657 A1 | 6/2013 | Leigh et al. | |
| 2013/0245362 A1 * | 9/2013 | Elofsson | 600/25 |
| 2013/0261377 A1 | 10/2013 | Adamson et al. | |
| 2013/0281764 A1 | 10/2013 | Bjorn et al. | |
| 2014/0064531 A1 | 3/2014 | Andersson et al. | |
| 2014/0121447 A1 | 5/2014 | Kasic et al. | |
| 2014/0121449 A1 | 5/2014 | Kasic et al. | |
| 2014/0121450 A1 | 5/2014 | Kasic et al. | |
| 2014/0121451 A1 | 5/2014 | Kasic et al. | |
| 2014/0121452 A1 | 5/2014 | Kasic et al. | |
| 2014/0140567 A1 * | 5/2014 | LeBoeuf et al. | 381/381 |
| 2014/0153737 A1 | 6/2014 | Geschiere | |
| 2014/0163692 A1 | 6/2014 | Van den Heuvel et al. | |
| 2014/0193011 A1 | 7/2014 | Parker | |
| 2014/0270293 A1 | 9/2014 | Ruppersberg et al. | |
| 2014/0275731 A1 | 9/2014 | Andersson et al. | |
| 2014/0275735 A1 | 9/2014 | Ruppersberg et al. | |
| 2014/0275736 A1 | 9/2014 | Ruppersberg et al. | |
| 2014/0336447 A1 | 11/2014 | Bjorn et al. | |
| 2015/0016649 A1 | 1/2015 | Van Himbeeck et al. | |
| 2015/0043766 A1 | 2/2015 | Westerkull | |
| 2015/0063616 A1 | 3/2015 | Westerkull | |
| 2015/0141740 A1 | 5/2015 | Miller | |
| 2015/0146902 A1 | 5/2015 | Jinton et al. | |
| 2015/0156594 A1 | 6/2015 | Bervoets | |

FOREIGN PATENT DOCUMENTS

| | | |
|---|---|---|
| WO | 2015/020753 A2 | 2/2015 |
| WO | 2015/034582 A2 | 3/2015 |

OTHER PUBLICATIONS

Poltawski et al "Relative transmissivity of ultrasound coupling agents commonly used by therapists in the UK." Ultrasound in Med. & Biol., vol. 33, No. 1, pp. 120-128, 2007. http://www.sciencedirect.com/science/article/pii/S0301562906017558.*

Mercola, "Alkaline Water: If You Fall for This "Water Fad" You Could Do Some Major Damage." pp. 1-6. Sep. 11, 2010. http://articles.mercola.com/sites/articles/archive/2010/09/11/alkaline-water-interview.aspx.*

Mettler Electronics Corp. "Sonigel ultrasound transmission gel material safety data sheet." Mar. 13, 2002. pp. 1-2. https://www.lakeland.edu/PDFs/MSDS/1392/Sonigel%20Ultrasound%20Gel%20(All%Brands).pdf.*

* cited by examiner

SYSTEMS, DEVICES, COMPONENTS AND METHODS FOR IMPROVED ACOUSTIC COUPLING BETWEEN A BONE CONDUCTION HEARING DEVICE AND A PATIENT'S HEAD OR SKULL

RELATED APPLICATIONS

This application is a continuation-in-part of, and claims priority and other benefits from each of the following U.S. Patent Applications: (a) U.S. patent application Ser. No. 13/550,581 entitled "Systems, Devices, Components and Methods for Bone Conduction Hearing Aids" to Pergola et al. filed Jul. 16, 2012 (hereafter "the '581 patent application"); (b) U.S. patent application Ser. No 13/650,026 entitled "Magnetic Abutment Systems, Devices, Components and Methods for Bone Conduction Hearing Aids" to Kasic et al. filed on Oct. 11, 2012 (hereafter "the '650 patent application"); (c) U.S. patent application Ser. No. 13/650,057 entitled "Magnetic Spacer Systems, Devices, Components and Methods for Bone Conduction Hearing Aids" to Kasic et al. filed on Oct. 11, 2012 (hereafter "the '057 patent application"), now U.S. Pat. No. 9 022 917; (d) U.S. patent application Ser. No. 13/650,080 entitled "Abutment Attachment Systems, Mechanisms, Devices, Components and Methods for Bone Conduction Hearing Aids" to Kasic et al. filed on Oct. 11, 2012 (hereafter "the '080 patent application"), (e) U.S. patent application Ser. No. 13/1649,934 entitled "Adjustable Magnetic Systems, Devices, Components and Methods for Bone Conduction Hearing Aids" to Kasic et al. filed on Oct. 11, 2012 (hereafter "the '934 patent application"); (f) U.S. patent application Ser. No. 13/804,420 entitled "Adhesive Bone Conduction Hearing Device" to Kasic et al. filed on Mar. 13, 2013 (hereafter "the '420 patent application"), now U.S. Pat. No. 9,031,274; (g) U.S. patent application Ser. No. 13/793,218 entitled "Cover for Magnetic Implant in a Bone Conduction Hearing Device System, and Corresponding Devices, Components and Methods" to Kasic et al. filed on Mar. 11, 2013 (hereafter "the '218 patent application"); (h) U.S. patent application Ser. No. 14/288,181 entitled "Sound Acquisition and Analysis Systems, Devices and Components for Magnetic Hearing Aids" to Ruppersberg et al. (hereafter "the '181 patent application"), and (i) (j) U.S. patent application Ser. No. 14/288,142 entitled "Implantable Sound Transmission Device for Magnetic Hearing Aid, and Corresponding Systems, Devices and Components" to Ruppersberg et al. (hereafter "the '288 patent application").

This application also claims priority and other benefits from U.S. Provisional Patent Application Ser. No. 61/970,336 entitled "Systems, Devices, Components and Methods for Magnetic Bone Conduction Hearing Aids" to Ruppersberg et al. filed on Mar. 25, 2014. Each of the foregoing patent applications is hereby incorporated by reference herein, each in its respective entirety.

FIELD OF THE INVENTION

Various embodiments of the invention described herein relate to the field of systems, devices, components, and methods for improving acoustic coupling of bone conduction hearing devices to patient's heads and skulls.

BACKGROUND

In some cases, an external magnetic "bone conduction hearing device" ("BCHD") is held in position on a patient's head by means of magnetic coupling that occurs between one or more magnetic members included in a baseplate or spacer of the BCHD and a magnetic implant that has been implanted beneath the patient's skin and affixed to the patient's skull. Acoustic signals originating from a transducer located in the external magnetic BCHD are transmitted through the baseplate or spacer (which is coupled to the transducer of the BCHD) and through the patient's skin to bone in the vicinity of the underlying magnetic implant, and then through the skull bone to the patient's cochlea. The acoustic signals generated and delivered by the transducer to the baseplate or spacer are provided in response to external ambient audio signals detected by one or more microphones disposed in external portions of the hearing aid, which are processed by a processor in the BCHD and provided to the transducer. The transmission of acoustic signals from the BCHD to the patient's bone occurs through skin and other tissue overlying the bone, and may also be through hair disposed between the baseplate or spacer and the magnetic implant.

In other cases, the BCHD is not secured to the patient's head through magnetic means, but instead is secured or attached to the patient's head by mechanical means, such as by a headband, a strap and/or adhesive.

Whether or not magnetic coupling means are employed to secure a BCHD to a patient's head or skull, a perennial difficulty has been the degree and quality of acoustic coupling that is capable of being achieved between a BCHD and a patient's skull or head. Poor acoustic coupling of EM transducer signals through a patient's skin and/or hair can occur, which results in substandard transmission of such signals to the patient's skull.

What is needed is a BCHD or BCHD system that somehow provides improved acoustic coupling between the BCHD and a patient's head or skull.

SUMMARY

In one embodiment, there is provided a method of improving acoustic coupling between a bone conduction hearing device (BCHD and a patient's head or skull, the BCHD comprising a transducer configured to generate sound signals for transmission to the patient's skull, the method comprising applying an aqueous gel or paste to a bottom surface of the BCHD, and attaching, securing or magnetically coupling the BCHD to or against the patient's head or skull, wherein at least portions of the gel or paste are operably disposed between the bottom surface of the BCHD and the patient's head or skull thereby to improve acoustic coupling and transmission of the sound signals generated the transducer to the patient's skull.

In another embodiment, there is provided a bone conduction hearing device (BCHD) comprising a transducer configured to generate sound signals for transmission to the patient's skull, a bottom surface, and an acoustic coupling gel or paste disposed on at least portions of the bottom surface, wherein when the BCHD is attached, secured or magnetically coupled to a patient's skull or head at least portions of the acoustic coupling gel or paste are disposed between the bottom surface and the patient's head or skull thereby to improve acoustic coupling and transmission of sound signals originating from the transducer to the patient's skull.

In yet another embodiment, there is provided a bone conduction hearing device (BCHD) kit comprising a BCHD comprising a transducer configured to generate sound signals for transmission to the patient's skull and a bottom surface, and an acoustic coupling gel or paste configured to be disposed on at least portions of the bottom surface, wherein when the BCHD is attached, secured or magnetically coupled to a patient's skull or head at least portions of the acoustic coupling gel or paste can be disposed between the bottom surface and the patient's head or skull thereby to improve acoustic coupling and transmission of sound signals originating from the transducer to the patient's skull.

In still another embodiment, there is provided an aqueous acoustic coupling gel or paste configured for use with a bone conduction hearing device (BCHD), the gel or paste comprising a substantially cross-linked system of one or more polymers, the gel having a viscosity sufficient to stick to a bottom surface of the BCHD after having been disposed thereon by a user, the BCHD comprising a transducer configured to generate sound signals for transmission to a patient's skull, wherein the gel is configured for use in conjunction with the BCHD by being disposed over at least portions of the bottom surface and between the bottom surface and the patient's skull when the BCHD is secured, attached or magnetically coupled to the patient's head or skull, and the gel is further configured to improve acoustic coupling and transmission of sound signals originating from the transducer to the patient's skull.

Further embodiments are disclosed herein or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for bone conduction and/or bone-anchored hearing aids.

A bone-anchored hearing aid ("BAHA"), also referred to as a bone conduction hearing device ("BCHD"), is an auditory prosthetic device based on bone conduction having a portion or portions thereof which are surgically implanted. A BAHA or BCHD uses the bones of the skull as pathways for sound to travel to a patient's inner ear. For people with conductive hearing loss, a BAHA or BCHD bypasses the external auditory canal and middle ear, and stimulates the still-functioning cochlea via an implanted metal post. For patients with unilateral hearing loss, a BAHA or BCHD uses the skull to conduct the sound from the deaf side to the side with the functioning cochlea. In some BAHA and BCHD systems, a titanium post or plate is surgically embedded into the skull with a small abutment extending through and exposed outside the patient's skin. A BAHA or BCHD sound processor attaches to the abutment and transmits sound vibrations through the external abutment to the implant. The implant vibrates the skull and inner ear, which stimulates the nerve fibers of the inner ear, allowing hearing. A BAHA or BCHD device can also be connected to an FM system or iPod by means of attaching a miniaturized FM receiver or Bluetooth connection thereto.

BAHA devices are manufactured by COCHLEAR™ of Sydney, Australia, and OTICON™ of Smoerum, Denmark. SOPHONO™ of Boulder, Colo. manufactures Alpha 1 and Alpha 2 magnetic BCHDs, which attach by magnetic means behind a patients ear to the patient's skull by coupling to a magnetic or magnetized bone plate (or "magnetic implant") implanted in the patient's skull beneath the skin.

Surgical procedures for implanting such posts or plates are relatively straightforward; and are well known to those skilled in the art. See, for example, "Alpha I (S) & Alpha I (M) Physician Manual—REV A S0300-00" published by Sophono, Inc, of Boulder, Colo. the entirety of which is hereby incorporated by reference herein.

Figure 1A:
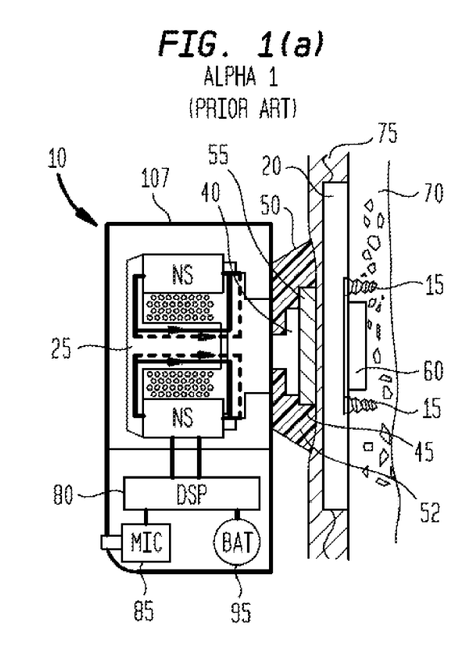
FIGS. 1(a), 1(b) and 1(c) show side cross-sectional schematic views of selected embodiments of prior art SOPHONO ALPHA 1, BAHA and AUDIANT bone conduction hearing aids, respectively.
Figure 1B:
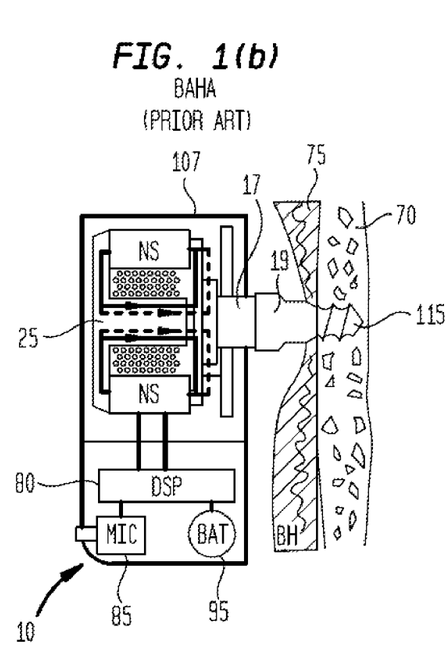
Figure 1C:
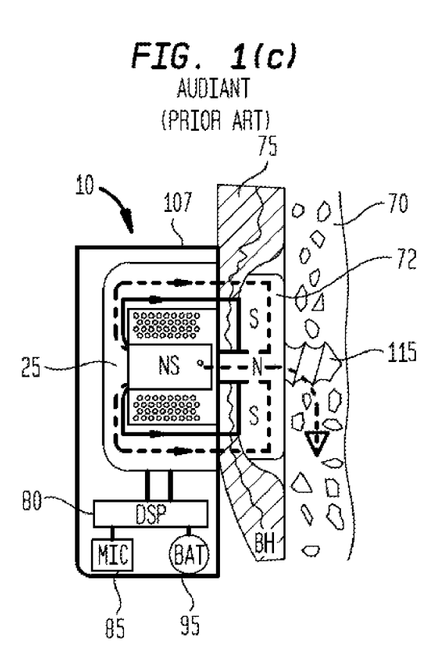

FIGS. 1(a), 1(b) and 1(c) show side cross-sectional schematic views of selected embodiments of prior art SOPHONO ALPHA 1, BAHA and AUDIANT bone conduction hearing aids, respectively. Note that FIGS. 1(b) and 1(c) not necessarily to scale.

Figure 2A:
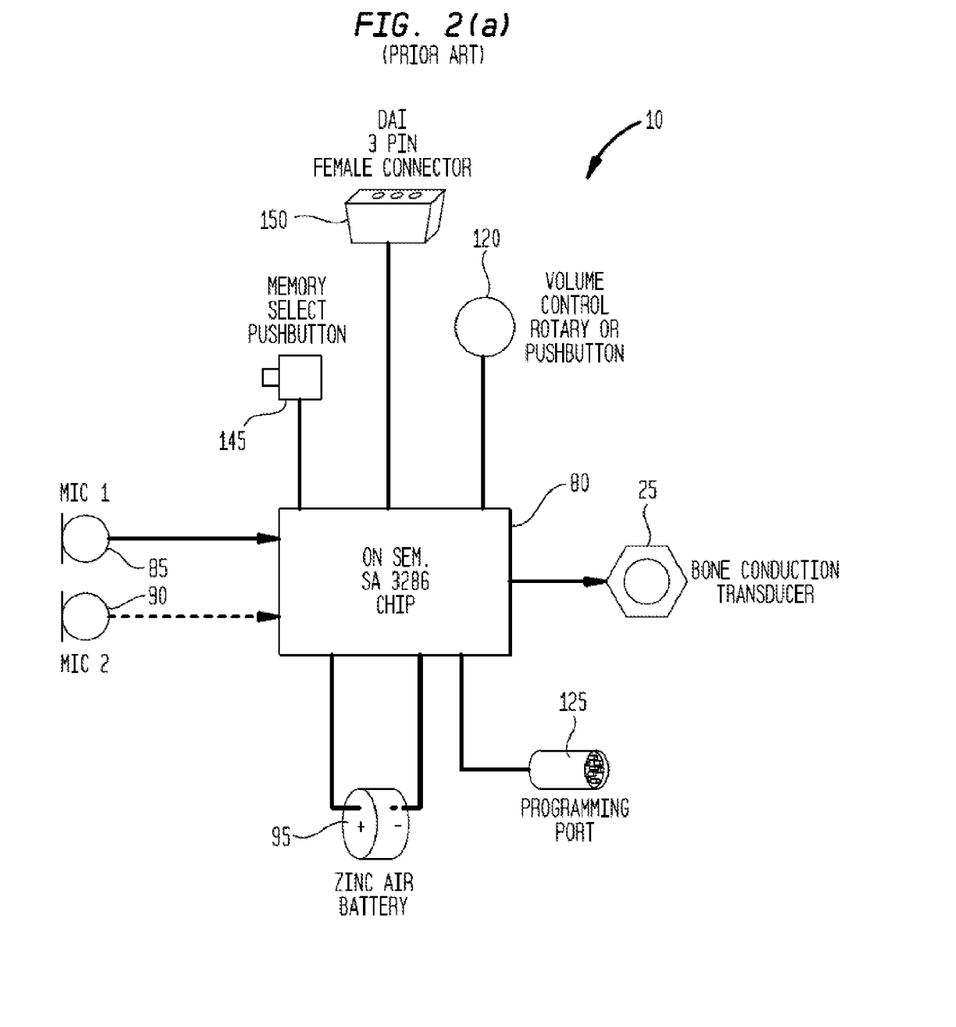
FIG. 2(a) shows one embodiment of a prior art functional electronic and electrical block diagram of hearing aid 10 shown in FIGS. 1(a) and 3(b)

In FIG. 1(a), magnetic hearing aid device 10 comprises housing 107, ectromagnetic/bone conduction ("EM") transducer 25 with corresponding magnets and coils, digital signal processor ("DSP") 80, battery 95, magnetic spacer 50, magnetic implant or magnetic implant bone plate 20. As shown in FIGS. 1(a) and 2(a), and according to one embodiment, magnetic implant 20 comprises a frame 21 (see FIG. 3(a)) formed of a biocompatible metal such as medical grade titanium that is configured to have disposed therein or have attached thereto implantable magnets or magnetic members 60. Bone screws 15 secure or affix magnetic implant 20 to skull 70, and are disposed through screw holes 23 positioned at the outward ends of arms 22 of magnetic implant frame 21 (see FIG. 2(a)). Magnetic members 60a and 60b are configured to couple magnetically to one or more corresponding external magnetic members or magnets 55 mounted onto or into, or otherwise forming a portion of, magnetic spacer or baseplate 50, which in turn is operably coupled to EM transducer 25 and metal disc 40. DSP 80 is configured to drive EM transducer 25, metal disk 40 and magnetic spacer or baseplate 50 in accordance with external audio signals picked up by microphone 85. DSP 80 and EM transducer 25 are powered by battery 95, which according to one embodiment may be a zinc-air battery, or may be any other suitable type of primary or secondary (i.e., rechargeable) electrochemical cell such as an alkaline or lithium battery.

As further shown in FIG. 1(a), magnetic implant 20 is attached to patient's skull 70, and is separated from magnetic spacer or baseplate 50 by patient's skin 75. Hearing aid device 10 of FIG. 1(a) is thereby operably coupled magnetically and mechanically to plate 20 implanted in patient's skull 70, which permits the transmission of audio signals originating in DSP 80 and EM transducer 25 to the patient's inner ear via skull 70.

FIG. 1(b) shows another embodiment of hearing aid 10, which is a BAHA device comprising housing 107, EM transducer 25 with corresponding magnets and coils, DSP 80, battery 95, external post 17, internal bone anchor 115, and abutment member 19. In one embodiment, and as shown in FIG. 1(b), internal bone anchor 115 includes a bone screw formed of a biocompatible metal such as titanium that is configured to have disposed thereon or have attached thereto abutment member 19, which in turn may be configured to mate mechanically or magnetically with external post 17, which in turn is operably coupled to EM transducer 25. DSP 80 is configured to drive EM transducer 25 and external post 17 in accordance with external audio signals picked up by microphone 85. DSP 80 and EM transducer 25 are powered by battery 95, which according to one embodiment is a zinc-air battery (or any other suitable battery or electrochemical cell as described above). As shown in FIG. 1(b), implantable bone anchor 115 is attached to patient's skull 70, and is also attached to external post 17 through abutment member 19, either mechanically or by magnetic means. Hearing aid device 10 of FIG. 1(b) is thus coupled magnetically and/or mechanically to bone anchor 115 implanted in patient's skull 70, thereby permitting the transmission of audio signals originating in DSP 80 and EM transducer 25 to the patient's inner ear via skull 70.

FIG. 1(c) shows another embodiment of hearing aid 10, which is an AUDIANT® type hearirmdevice, where an implantable magnetic member 72 is attached by means of bone anchor 115 to patient's skull 70. Internal bone anchor 115 includes a bone screw formed of a biocompatible metal such as titanium, and has disposed thereon or attached thereto implantable magnetic member 72, which couples magnetically through patient's skin 75 to EM transducer 25. Processor 80 is configured to drive EM transducer 25 in accordance with external audio signals picked up by microphone 85. Hearing aid device 10 of FIG. 1(c) is thus coupled magnetically to bone anchor 115 implanted in patient's skull 70, thereby permitting the transmission of audio signals originating in processor 80 and EM transducer 25 to the patient's inner ear via skull 70.

Figure 2B:
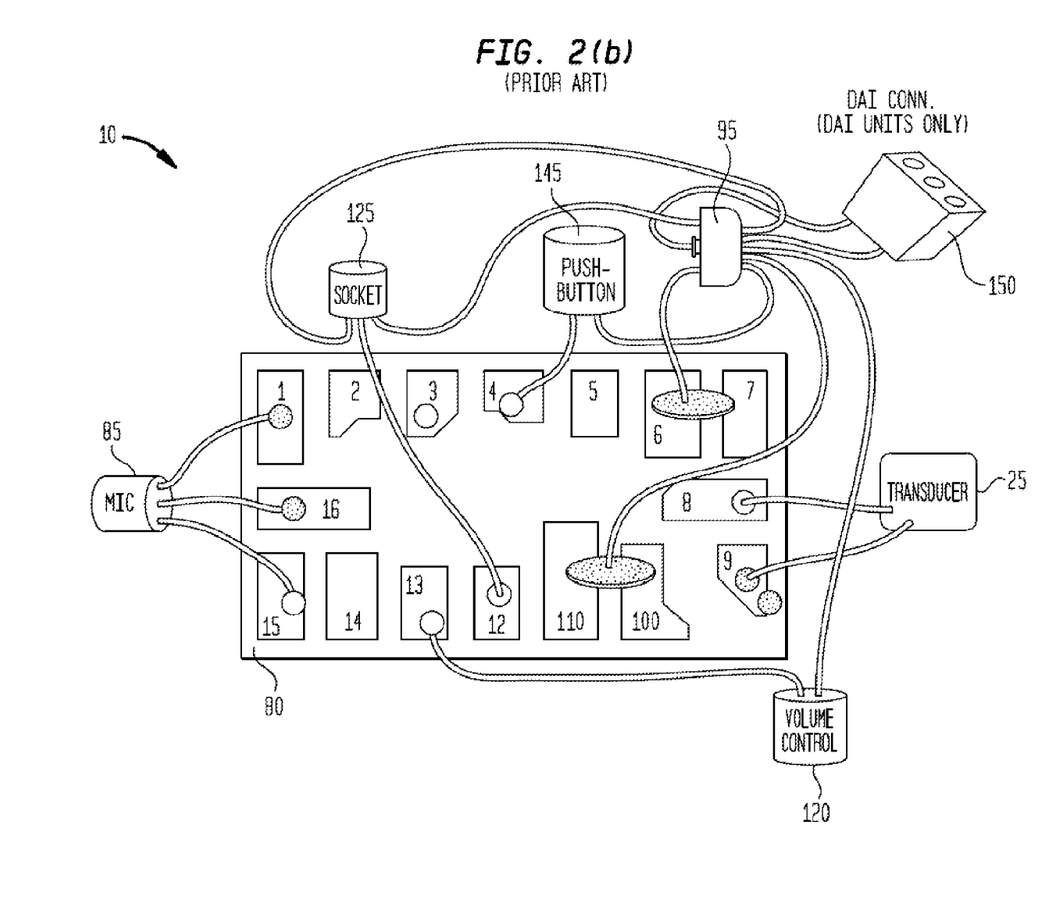
FIG. 2(b) shows one embodiment of a prior art wiring diagram for a SOPHONO ALPHA 1 hearing aid manufactured using an SA3286 DSP.

FIG. 2(a) shows one embodiment of a prior art functional electronic and electrical block diagram of hearing aid 10 shown in FIGS. 1(a) and 2(b). In the block diagram of FIG. 2(a), and according to one embodiment, processor 80 is a SOUND DESIGN TECHNOLOGIES® SA3286 INSPIRA EXTREME® DIGITAL DSP, for which data sheet 48550-2 dated March 2009, filed on even date herewith in an accompanying Information Disclosure Statement ("IDS"), is hereby incorporated by reference herein in its entirety. The audio processor for the SOPHONO ALPHA 1 hearing aid is centered around DSP chip 80, which provides programmable signal processing. The signal processing may be customized by computer software which communicates with the Alpha through programming port 125. According to one embodiment, the system is powered by a standard zinc air battery 95 (i.e. hearing aid battery), although other types of batteries may be employed. The SOPHONO ALPHA 1 hearing aid detects acoustic signals using a miniature microphone 85. A second microphone 90 may also be employed, as shown in FIG. 2(a). The SA 3286 chip supports directional audio processing with second microphone 90 to enable directional processing. Direct Audio Input (DAI) connector 150 allows connection of accessories which provide an audio signal in addition to or in lieu of the microphone signal. The most common usage of the DAI connector is FM systems. The FM receiver may be plugged into DAI connector 150. Such an FM transmitter can be worn, for example, by a teacher in a classroom to ensure the teacher is heard clearly by a student wearing hearing aid 10. Other DAI accessories include an adapter for a music player, a telecoil, or a Bluetooth phone accessory. According to one embodiment, processor 80 or SA 3286 has 4 available program memories, allowing a hearing health professional to customize each of 4 programs for different listening situations. The Memory Select Pushbutton 145 allows the user to choose from the activated memories. This might include special frequency adjustments for noisy situations, or a program which is Directional, or a program which uses the DAI input.

FIG. 2(b) shows one embodiment of a prior art wiring diagram for a SOPHONO ALPHA 1 hearing aid manufactured using the foregoing SA3286 DSP. Note that the various embodiments of hearing aid 10 are not limited to the use of a SA3286 DSP, and that any other suitable CPU, processor, controller or computing device may be used. According to one embodiment, processor 80 is mounted on a printed circuit board 155 disposed within housing 107 of hearing aid 10.

In some embodiments, the microphone incorporated into hearing aid 10 is an 8010T microphone manufactured by SONION®, for which data sheet 3800-3016007, Version 1 dated December, 2007, filed on even date herewith in the accompanying IDS, is hereby incorporated by reference herein in its entirety. In the various embodiments of hearing aids claimed herein, other suitable types of microphones, including other types of capacitive microphones, may be employed.

In still further embodiments of hearing aids claimed herein, electromagnetic transducer 25 incorporated into hearing aid 10 is a VKH3391W transducer manufactured by BMH-Tech® of Austria, for which the data sheet filed on even date herewith in the accompanying IDS is hereby incorporated by reference herein in its entirety. Other types of suitable EM or other types of transducers may also be used.

Figure 3A:
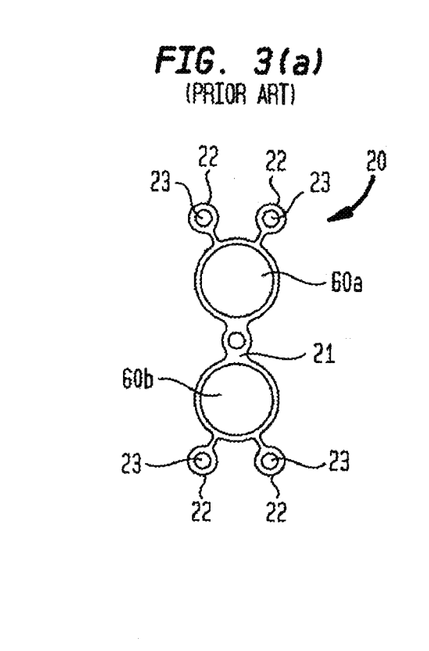
FIG. 3(a) shows one embodiment of prior art magnetic implant 20 according to FIG. 1(a)
Figure 3B:
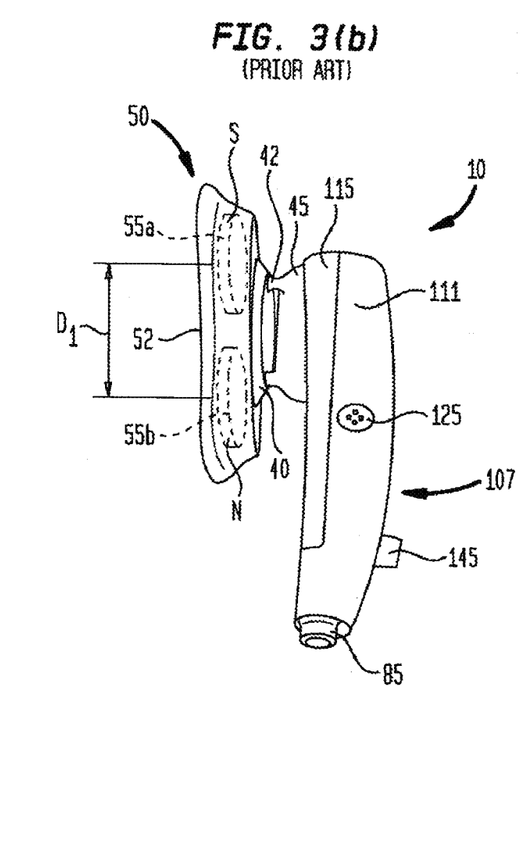
FIG. 3(b) shows one embodiment of a prior art SOPHONO® ALPHA 1® hearing aid 10.
Figure 3C:
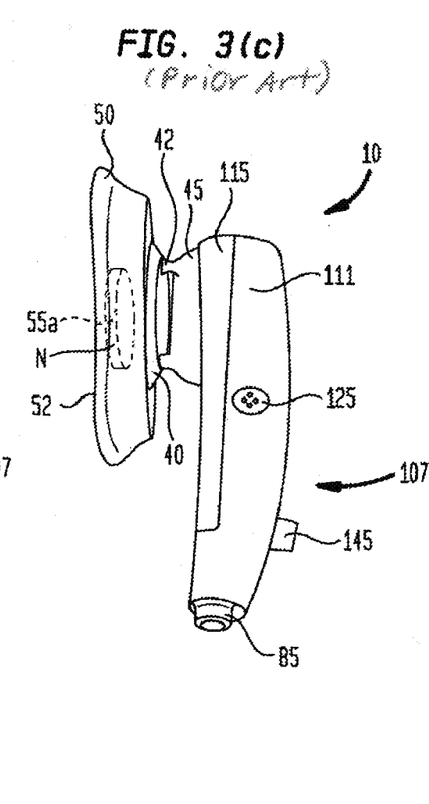
FIG. 3(c) shows another embodiment of a prior art SOPHONO® ALPHA® 1 hearing aid 10.

FIGS. 3(a), 3(b) and 3(c) show implantable bone plate or magnetic implant 20 in accordance with FIG. 1(a), where frame 22 has disposed thereon or therein magnetic members 60a and 60b, and where magnetic spacer or baseplate 50 of hearing aid 10 has magnetic members 55a and 55b spacer disposed therein. The two magnets 60a and 60b of magnetic implant 20 of FIG. 2(a) permit hearing aid 10 and magnetic spacer 50 to be placed in a single position on patient's skull 70, with respective opposing north and south poles of magnetic members 55a, 60a, 55b and 60b appropriately aligned with respect to one another to permit a sufficient degree of magnetic coupling to be achieved between magnetic spacer 50 and magnetic implant 20 (see FIG. 3(b)). As shown in FIG. 1(a), magnetic implant 20 is preferably configured to be affixed to skull 70 under patient's skin 75. In one aspect, affixation of magnetic implant 20 to skull 75 is by direct means, such as by screws 15. Other means of attachment known to those skilled in the art are also contemplated, however, such as glue, epoxy, and sutures.

Referring now to FIG. 3(b), there is shown a SOPHONO® ALPHA 1® hearing aid 10 configured to operate in accordance with magnetic implant 20 of FIG. 3(*a*). As shown, hearing aid 10 of FIG. 3(*b*) comprises upper housing 111, lower housing 115, magnetic spacer 50, external magnets 55*a* and 55*b* disposed within spacer 50, EM transducer diaphragm 45, metal disk 40 connecting EM transducer 25 to spacer 50, programming port/socket 125, program switch 145, and microphone 85. Not shown in FIG. 3(*b*) are other aspects of the embodiment of hearing aid 10, such as volume control 120, battery compartment 130, battery door 135, battery contacts 140, direct audio input (DAI) 150, and hearing aid circuit board 155 upon which various components are mounted, such as processor 80.

Continuing to refer to FIGS. 3(*a*) and 3(*b*), frame 22 of magnetic implant 20 holds a pair of magnets 60*a* and 60*b* that correspond to magnets 55*a* and 55*b* included in magnetic spacer o baseplate 50 shown in FIG. 3(*b*). The south (S) pole and north (N) poles of magnets 55*a* and 55*b*, are respectively configured in spacer or baseplate 50 such that the south pole of magnet 55*a* is intended to overlie and magnetically couple to the north pole of magnet 60*a*, and such that the north pole of magnet 55*b* is intended to overlie and magnetically couple to the south pole of magnet 60*b*. This arrangement and configuration of magnets 55*a*, 55*b*, 60*a* and 60*b* is intended permit the magnetic forces required to hold hearing aid 10 onto a patient's head to be spread out or dispersed over a relatively wide surface area of the patient's hair and/or skin 75, and thereby prevent irritation of soreness that might otherwise occur if such magnetic forces were spread out over a smaller or more narrow surface area. In the embodiment shown in FIG. 3(*a*), frame 22 and magnetic implant 20 are configured for affixation to patient's skull 70 by means of screws 15, which are placed through screw recesses or holes 23. FIG. 3(*c*) shows an embodiment of hearing aid 10 configured to operate in conjunction with a single magnet 60 disposed in magnetic implant 20 per FIG. 1(*a*).

Figure 4A:
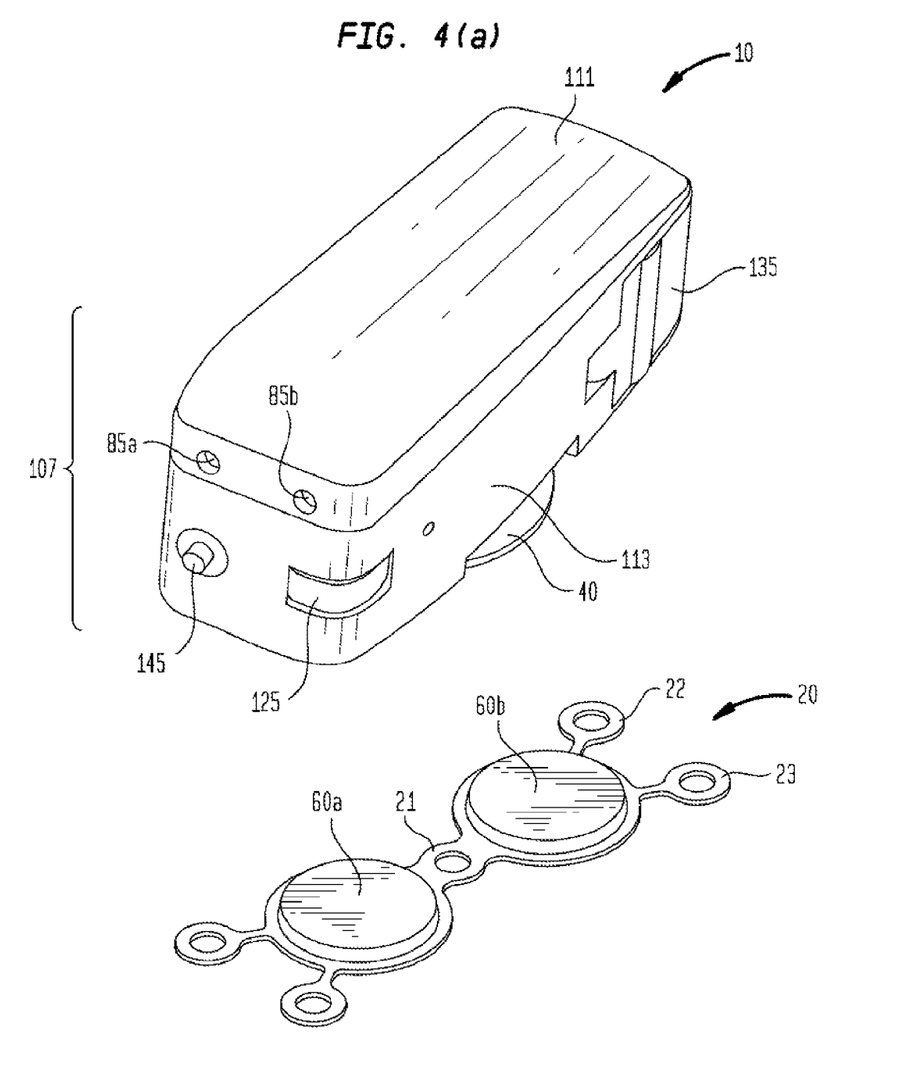
FIGS. 4(a) and 4(b) show various aspects and views of a SOPHONO® ALPHA® 2 MPO hearing aid 10.
Figure 4B:
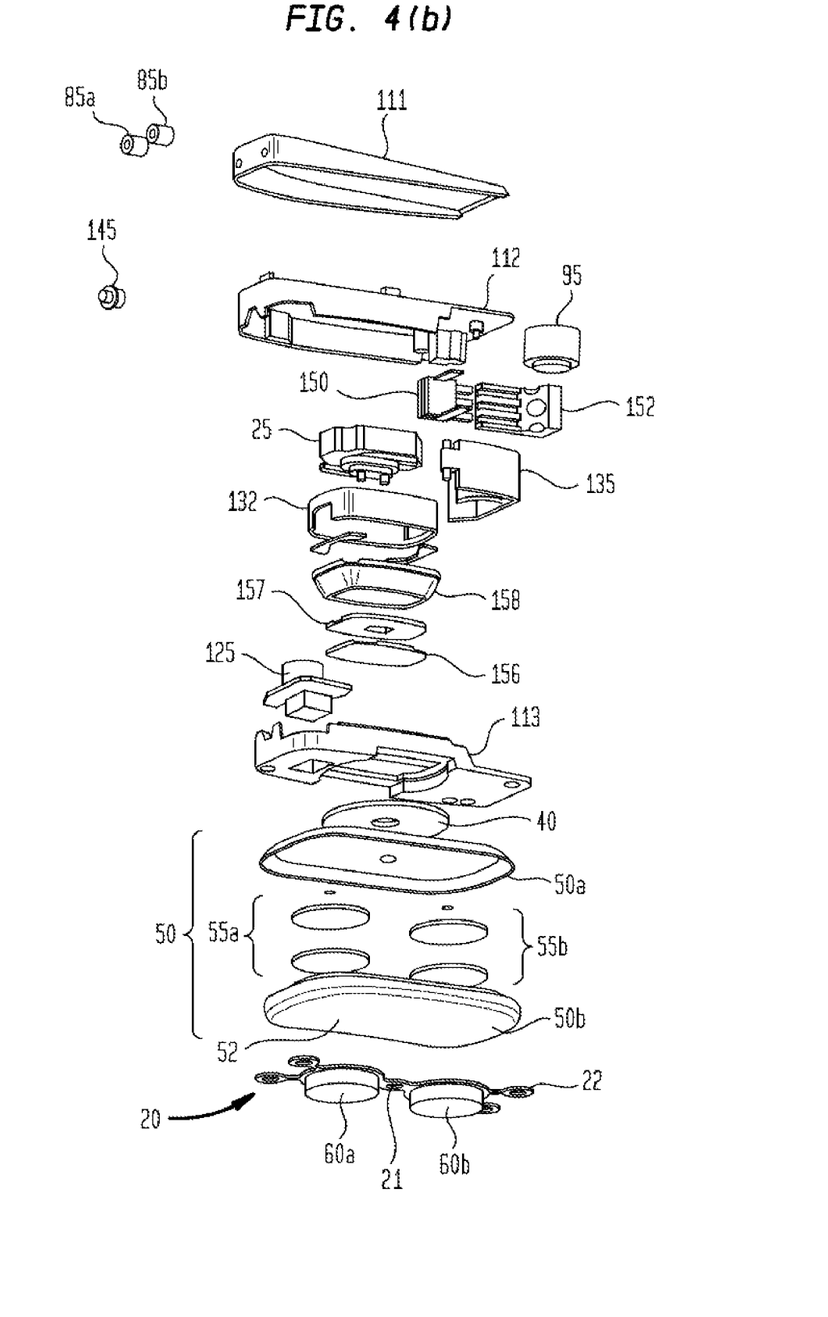

Referring now to FIGS. 4(*a*) and 4(*b*), there are shown perspective and exploded views of a SOPHONO Alpha 2 MPO BCHD 10. In FIG. 4(*a*), there is shown a top right perspective view of one embodiment of a magnetic BCHD 10 and corresponding magnetic implant 20. In FIG. 4(*b*), there is shown an exploded bottom perspective view of BCHD 10 of FIG. 4(*a*), with the various components thereof described above shown therein. Baseplate or magnetic spacer 50 of FIG. 4(*b*) comprises external magnets 55*a* and 55*b*, which are sandwiched between upper and lower portions 50*a* and 50*b* of baseplate or spacer 50, and which according to one embodiment are held in place within baseplate 50 by silicone. As further shown in FIG. 4(*b*), transducer 25, which according to one embodiment is an electromagnetic ("EM") transducer, but which according to other embodiments is a piezoelectric transducer, is held by clamp 132 within housing 107 and suspended therein by suspension parts 156, 157 and 158.

Figure 5A:
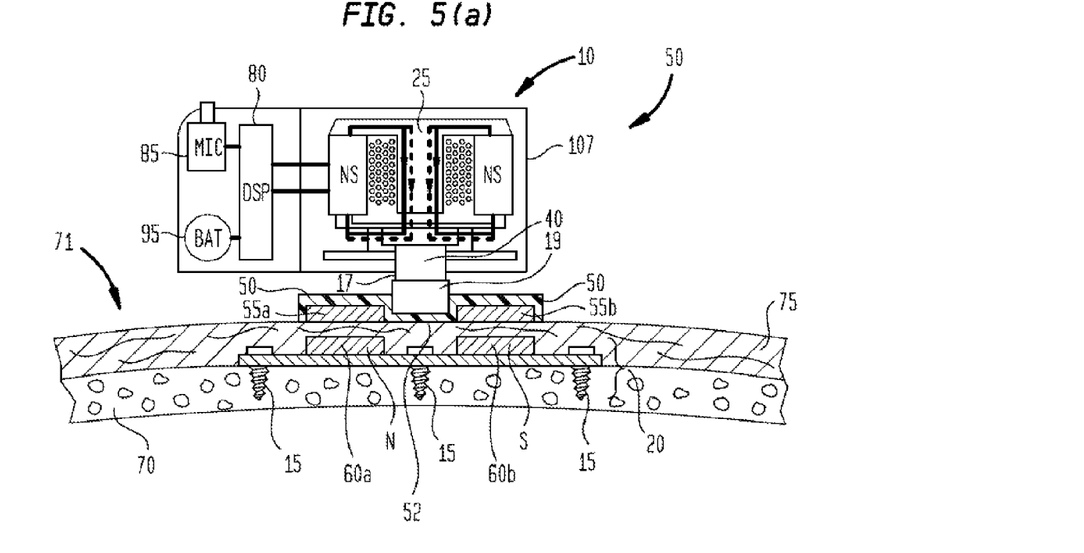
FIGS. 5(a) and 5(b) show two different embodiments of a magnetic BCHD 10 coupled to a patient's head 71, with and without paste or gel 12.
Figure 5B:
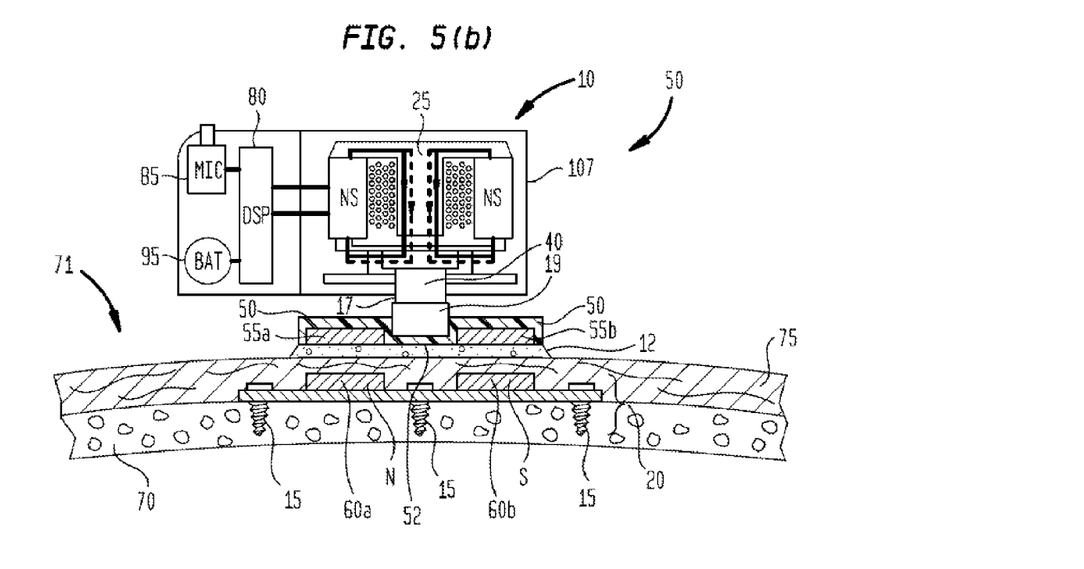
Figure 7:
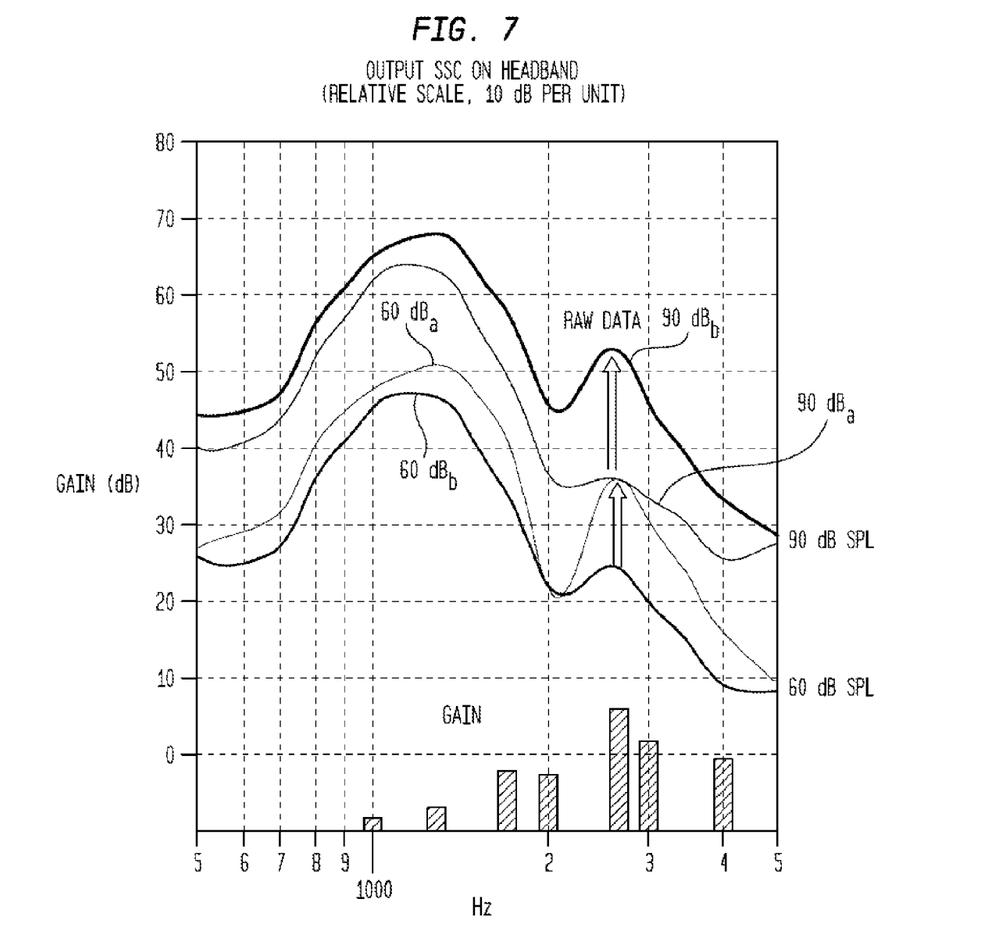
FIG. 7 shows comparative test data obtained with and without the use of a gel or paste 12 when coupling a BCHD 10 mechanically to a patient's head 71.

FIGS. 5(*a*) through 7 show various aspects of a gel or paste 12, which is employed to improve acoustic coupling between a BCHD 10 and a patient's head 71 and/or skull 70. Referring now to FIGS. 5(*a*) and 5(*b*), there are shown two different embodiment of a magnetic BCHD 10 operably and magnetically coupled to magnetic implant 20 implanted in patient's head 71 and skull 70 beneath skin patient's skin 75. In FIG. 5(*a*), bottom surface 52 of baseplate or magnetic spacer 50 magnetic BCHD 10 is directly in contact with patient's skin 75. In FIG. 5(*b*), bottom surface 52 of baseplate or magnetic spacer 50 magnetic BCHD 10 is in contact with gel or paste 12, which is disposed between bottom surface 52 and patient's skin 75. Gel or paste 12 of FIG. 5(*b*) is configured and formulated to improve acoustic coupling between BCHD 10 and a patient's head 71 and/or skull 70.

Figure 6A:
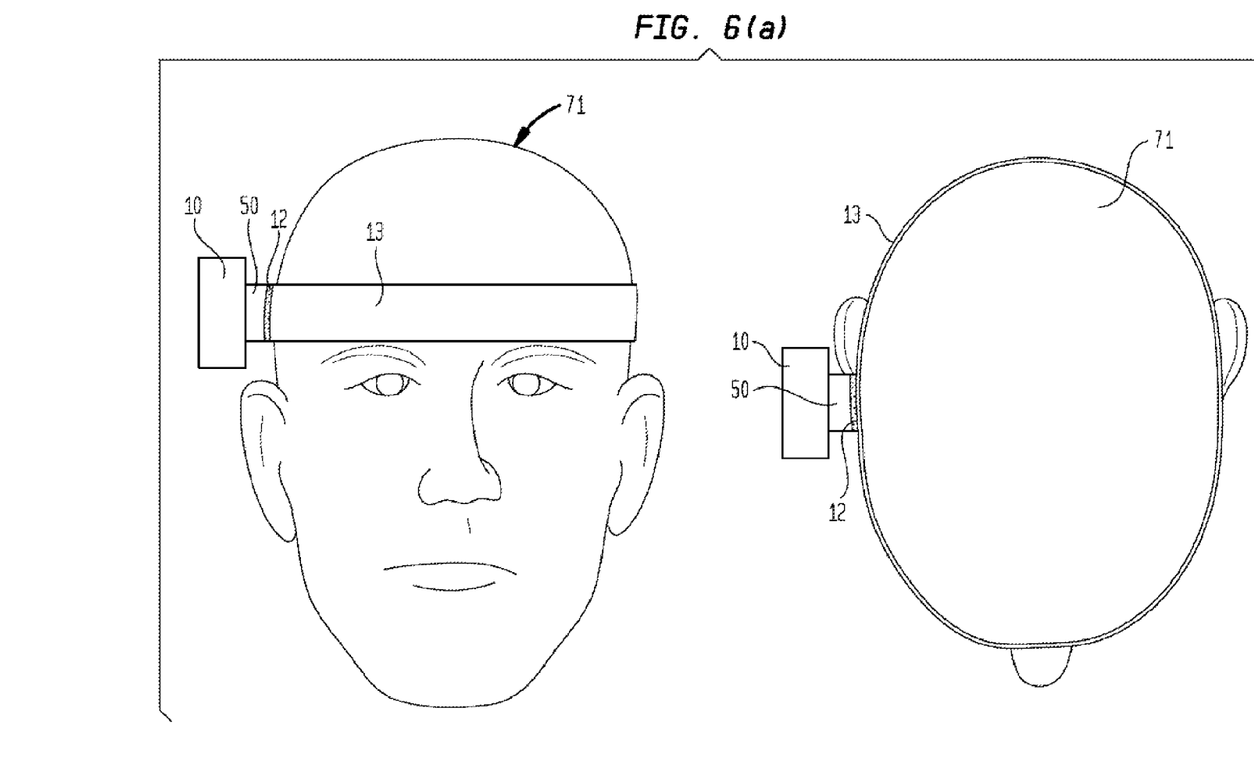
FIGS. 6(a) and 6(b) show various embodiments of a BCHD 10 mechanically secured or coupled to a patient's head 71 by a headstrap 13, with the use of a gel or paste 13.
Figure 6B:
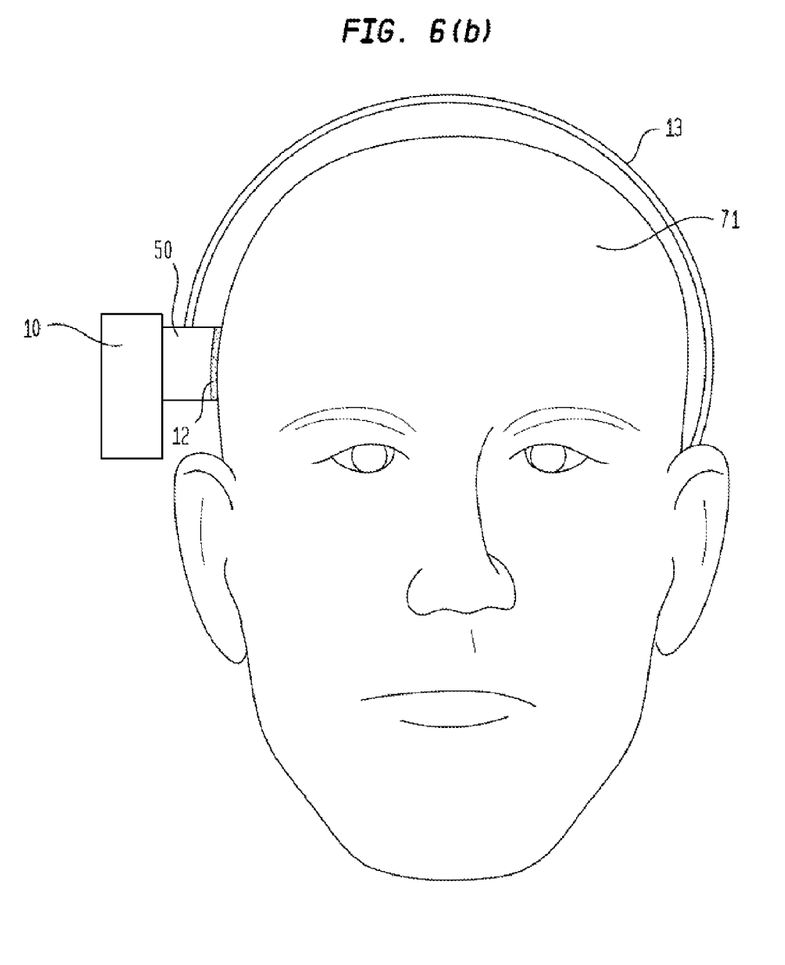

Similarly, gel or paste 12 may be employed in conjunction with a non-magnetic or other type of BCHD 10, as shown in FIGS. 6(*a*) and 6(*b*), where BCHD is secured or attached to patient's head 71 by headstrap 13, and gel or paste 12 is disposed between BCHD 10 and the patient's head 71, thereby to improve acoustic coupling between BCHD 10 and a patient's head 71 and/or skull 70.

FIGS. 5(*b*) through 6(*b*) illustrate a method of improving acoustic coupling between a BCHD 10 and a patient's head 71 or skull 70, where BCHD 10 comprises a transducer (e.g., of the EM or piezoelectric types) configured to generate sound signals for transmission to patient's skull 70. The method comprises applying an aqueous gel or paste 12 to a bottom surface 52 of BCHD 10, and attaching, securing or magnetically coupling BCHD 10 to or against the patient's head 71 or skull 70. At least portions of gel or paste 12 are operably disposed between the bottom surface 52 of BCHD 10 and the patient's head 71 or skull 70, thereby to improve acoustic coupling and transmission of the sound signals generated transducer 25 to patient's skull 70.

In some embodiments, baseplate or spacer 50 is operably connected to or forms a portion of BCHD 10, and the baseplate or spacer is operably attached to or forms a portion of transducer 25. Transducer 25, by way of non-limiting example, may be an electromagnetic ("EM") transducer or a piezoelectric transducer. BCHD 10 may be a magnetic BCHD or a non-magnetic BCHD. BCHD 10 may be attached or secured to patient's skull 70 or head 71 with at least one of a strap, a headstrap 13, a band, a head band, a clip, a hair clip, and/or an adhesive. Baseplate or spacer 50 may also be incorporated into a strap, a headstrap 13, a band, a head band, a clip, a hair clip, and/or a substrate comprising an adhesive. BCHD 10 may be attached to such a strap, a headstrap 13, a band, a head band, a clip, a hair clip, and/or a substrate by any number of suitable means, such as a snap or other suitable connecting or attachment means. Examples of headbands that may be adapted for use with gel or paste 12 include the PONTO soft band manufactured by Oticon and the BAHA softband manufactured by Cochlear.

In one embodiment, gel or paste 12 is a water-soluble gel. Gel 12 may comprise at least one of one or more of a cross-linked polyacrylate polymer, polyalkenyl ether, divinyl glycol propylene, glycol, glycerin, a carbomer, a carbopol, theolamine, water, demineralized water, distilled water, aloe vera, carrageenan, EDTA (Ethylenediaminetetraacetic acid), salt, vitamin E, a preservative, a thickening agent, and a neutralizer. Gel 12 may have a pH between about 5.5 and about 6.5, and may also be any one or more of substantially colorless, hypoallergenic, non-sterile, bacteriostatic, non-sensitizing to human skin, non-irritating to human skin, biocompatible, orally compatible, and ingestible. In some embodiments, the sound velocity of gel 12 ranges between about 1,450 meters/second and about 1,700 meters/second, and the viscosity of gel 12 ranges between about 10 Pascal-seconds and about 20 Pascal-seconds. In one embodiment, the viscosity of gel 12 is sufficient to remain attached to baseplate or spacer 50 when applied thereon in a layer having a thickness ranging between about 1 mm and about 2 mm. (Other thicknesses of gel 12 on bottom surface 52 of baseplate 50 are also contemplated.) Gel 12 may have an acoustic impedance substantially similar to soft human body tissue.

According to its various embodiments, gel or paste 12 fills voids or spaces that might otherwise be filled or created by air, hair, skin wrinkles or irregularities, and/or skin surfaces, which improves the efficiency of the transmission of sound signals from transducer 25 to the patient's skull 70. Using gel or paste 12, sound signals are transmitted largely or substantially through an acoustically efficient coupling medium (i.e., paste or gel 12) disposed between bottom surface 52 of baseplate or spacer 50 and patient's skin 75. Gel or paste 12 improves the transmission of sound energy, because sound is not effectively transmitted through air or hair. Aside from attenuation effects, air and hair can present severe acoustic impedance mismatches with respect to BCHD 10 and skin 75. Even an extremely thin air gap between bottom surface 52 of BCHD 10 or headstrap 13 and the patient's skin 75 can prevent efficient sound energy transmission to patient's skull 70.

Referring now to FIG. 7, there are shown experimental results obtained with a non-magnetic BCHD secured to a patient's head by a headstrap 13, both with and without the use of a gel 12 disposed between a baseplate 50 and the patient's skin and hair on her head 71. The gel employed to obtain the results shown in FIG. 7 comprised an aqueous solution comprising 2% Carbomer 940 polymer. The gel comprised 10 grams of carbomer 940 polymer, 0.25 grams of EDTA, 750 grams of propylene glycol, 12.5 grams of theolamine, and 500 ml of distilled water. The BCHD employed was a SOPHONO Alpha 2 MPO device without magnetic coupling means attached thereto, where BCHD 10 was attached directly to a headband 13. Gel 12 was disposed between a bottom surface 52 of headband 13 and the patient's skin 75 and hair on her head 71. In FIG. 7, input signals are shown in sound pressure levels (SPLs) expressed in decibels (vertical axis) versus sound signal frequency (horizontal axis), for varying tones. As shown in FIG. 7, acousto-mechanical gain for sound signals improved markedly at two different input signal levels of 60 and 90 dB when gel was applied to bottom surface 52 of headband 13 (i.e., from 60 $dB_a$ to 60 $dB_b$, and from 90 $dB_a$ to 90 $dB_b$). Thus, and as shown in FIG. 7, gel or paste 12 improves high frequency sound signal transmission, and also permits lower magnetic forces to be employed when magnetically coupling a magnetic BCHD to a patient's skull 70. Magnetic coupling forces as low as 0.5 N may be sufficient due to the stickiness provided by gel or paste 12. Lower magnetic headband forces could result in fewer side effects for patients, and reduced patient pain over long-term use.

Those skilled in the art will now understand that many different permutations, combinations and variations of gel or paste 12, and of BCHD 10, headstrap, clip or attachment means 13, baseplate or spacer 50, and other components of a BCHD system fall within the scope of the various embodiments. Those skilled in the art will now appreciate that many different combinations, permutations and configurations of gels, pastes, baseplates, spacers, headstraps, magnetic implants and BCHDs covers may be employed to arrive at suitable configurations of same. For example, the bottom surfaces 52 of baseplates or spacers 50 may be modified to retain or hold a gel or paste 12 therein by way of ridges or grooves provided therein, or an adhesive patch may be configured to hold a gel or paste thereon and secure a BCHD to a patient's skin or hair. Moreover, the above-described embodiments should be considered as examples, rather than as limiting the scopes thereof.

We claim:

1. A method of improving acoustic coupling between a bone conduction hearing device (BCHD) and a patient's head or skull, the BCHD comprising a transducer configured to generate sound signals for transmission to the patient's skull, the method comprising applying an aqueous acoustically conductive gel or paste to a bottom surface of the BCHD, and attaching, securing or magnetically coupling the BCHD to or against the patient's head or skull; wherein at least portions of the acoustically conductive gel or paste are operably disposed between the bottom surface of the BCHD and the patient's head or skull thereby to improve acoustic coupling and transmission of the audible frequency components of sound signals generated by the transducer to the patient's skull, wherein the acoustically conductive gel or paste is water soluble, wherein the transducer is an electromagnetic ("EM") transducer, wherein the sound velocity of the acoustically conductive gel or paste ranges between 1,450 meters/second and 1,700 meters/second, wherein a baseplate or spacer is operably connected to or forms a portion of the BCHD and is operably attached to or forms a portion of the transducer, and wherein the acoustically conductive gel or paste has a pH between 5.5 and 6.5.

2. The method of claim 1, wherein the BCHD further comprises a piezoelectric transducer.

3. The method of claim 1, wherein the BCHD is a magnetic BCHD.

4. The method of claim 3, wherein a magnetic implant is attached to or in the patient's skull beneath the patient's skin at an implant location, and is configured to magnetically couple to the magnetic BCHD.

5. The method of claim 4, wherein the magnetic BCHD is magnetically attached to the patient's skull over the implant location.

6. The method of claim 1, further comprising attaching or securing the BCHD to the patient's skull or head with at least one of a strap, a head strap, a band, a clip, and a hair clip.

7. The method of claim 1, wherein the acoustically conductive gel or paste comprises at least one of one or more of a cross-linked polyacrylate polymer, polyalkenyl ether, divinyl glycol propylene, glycol, glycerin, a carbomer, a carbopol, theolaimne, aloe vera, carrageenan, EDTA (Ethylenediaminetetraacetic acid), salt, vitamin E, a preservative, a thickening agent, and a neutralizer.

8. The method of claim 1, wherein the acoustically, conductive gel or paste is at least one of colorless, non-sterile, bacteriostatic, non-sensitizing to human skin, non-irritating to human skin, biocompatible, orally compatible, and ingestible.

9. The method of claim 1, wherein the viscosity of the acoustically conductive gel or, paste ranges between 10 Pascal-seconds and 20 Pascal-seconds.

10. The method of claim 1, wherein the viscosity of the acoustically conductive gel or, paste is sufficient to remain attached to the baseplate or spacer when applied thereon in a layer having a thickness ranging between 1 mm and 2 mm.

11. The method of claim 1, wherein the acoustically conductive gel or paste has an acoustic impedance similar to soft human body tissue.

12. A bone conduction hearing device (BCHD), comprising:
a transducer configured to generate sound signals for transmission to the patient's skull;
a bottom surface, and an acoustically conductive gel or paste disposed on at least portions of the bottom surface; wherein when the BCHD is attached, secured or magnetically coupled to a patient's skull or head at least portions of the acoustically conductive gel or paste are disposed between the bottom surface and the patient's head or skull thereby to improve acoustic coupling and transmission of the audible frequency components of sound signals originating from the transducer to the patient's skull, wherein the transducer is an electromagnetic ("EM") to transducer, wherein the acoustically conductive gel or paste is water soluble, wherein the sound velocity of the acoustically conductive gel or paste ranges between 1,450 meters/second and 1,700 meters/second, wherein a baseplate or spacer is operably connected to or forms a portion of the BCHD, and the baseplate or spacer is operably attached to or forms a portion of the transducer, and wherein the acoustically conductive gel or paste has a pH between 5.5 and 6.5.

13. The BCHD of claim 12, further comprising a piezoelectric transducer.

14. The BCHD of claim 12, wherein a magnetic implant is attached to or in the patient's skull beneath the patient's skin at an implant location, and is configured to magnetically couple to the magnetic BCHD.

15. The BCHD of claim 14, wherein the magnetic BCHD is configured to be magnetically attached to the patient's skull over the implant location.

16. The BCHD of claim 12, further comprising at least one of a strap, a head strap, la band, a clip, and a hair clip configured to attach or secure the BCHD to the patient's skull or head.

17. The BCHD of claim 12, wherein the acoustically conductive gel or paste comprises at least one of one or more of a cross-linked polyacrylate polymer, polyalkenyl ether, divinyl glycol propylene, glycol, glycerin, a carbomer, a carbopol, theolamme, aloe vera, carrageenan, EDTA (Ethylenediaminetetraacetic acid), salt, vitamin E, a preservative, a thickening agent, and a neutralizer.

18. The BCHD of claim 12, wherein the acoustically conductive gel or paste is at least one of colorless, non-sterile, bacteriostatic, non-sensitizing to human skin, nonirritating to human skin, biocompatible, orally compatible, and ingestible.

19. The BCHD of claim 12, wherein the viscosity of the acoustically conductive gel or paste ranges between 10 Pascal-seconds and 20 Pascal-seconds.

20. The BCHD of claim 12, wherein the viscosity of the acoustically conductive gel or paste is sufficient to remain attached to the baseplate or spacer when applied thereon in a layer having a thickness ranging between 1 mm and 2 mm.

21. The BCHD of claim 12, wherein the acoustically conductive gel or paste has an acoustic impedance similar to soft human body tissue.

22. A bone conduction hearing device (BCHD) kit, comprising:
a BCHD comprising a transducer configured to generate sound signals for transmission to the patient's skull and a bottom surface, and an acoustically conductive gel or paste configured to be disposed on at least portions of the bottom surface; wherein when the BCHD is attached, secured or magnetically coupled to a patient's skull or head at least portions of the acoustically conductive gel or paste can be disposed between the bottom surface and the patient's head or skull thereby to improve acoustic coupling and transmission of the audible frequency components of sound signals originating from the transducer to the patient's skull, wherein the transducer is an electromagnetic ("EM") transducer, wherein the acoustically conductive gel or paste is water soluble, wherein the sound velocity of the acoustically conductive gel or paste ranges between 1,450 meters/second and 1,700 meters/second, wherein a baseplate or spacer is operably connected to or forms a portion of the BCHD and the baseplate or spacer is operably attached to or forms a portion of the transducer, and wherein the acoustically conductive gel or paste has a pH between 5.5 and 6.5.

23. The BCHD kit of claim 22, further comprising a piezoelectric transducer.

24. The BCHD kit of claim 23, further comprising a magnetic implant configured to be attached to or in the patient's skull beneath the patient's skin at an implant location, and for magnetic coupling to the magnetic BCHD.

25. The BCHD kit of claim 24, wherein the magnetic BCHD is configured to be magnetically attached to the patient's skull over the implant location.

26. The BCHD kit of claim 22, further comprising at least one of a strap, a head strap, a band, a clip, and a hair clip configured to attach or secure the BCHD to the patient's skull or head.

27. The BCHD kit of claim 22, wherein the acoustically conductive gel or paste comprises at least one of one or more of a cross-linked polyacrylate polymer, polyalkenyl ether, divinyl glycol propylene, glycol, glycerin, a carbomer, a carbopol, theolamine, aloe vera, carrageenan, EDTA (Ethylenediaminetetraacetic acid), salt, vitamin E, a preservative, a thickening agent, and a neutralizer.

28. The BCHD kit of claim 22, wherein the acoustically conductive gel or paste is at least one of colorless, non-sterile, bacteriostatic, non-sensitizing to human skin, non-irritating to human skin, biocompatible, orally compatible, and ingestible.

29. The BCHD kit of claim 22, wherein the viscosity of the acoustically conductive gel or paste ranges between 10 Pascal-seconds and 20 Pascal-seconds.

30. The BCHD kit of claim 22, wherein the viscosity of the acoustically conductive gel or paste is sufficient to remain attached to the baseplate or spacer when applied thereon in a layer having a thickness ranging between 1 mm and 2 mm.

31. The BCHD kit of claim 22, wherein the acoustically conductive gel or paste has an acoustic impedance similar to soft human body tissue.

32. An aqueous acoustically conductive gel or paste configured for use with a bone conduction hearing device (BCHD), the acoustically conductive gel or paste comprising a cross-linked system of one or more polymers, the acoustically conductive gel or paste having a viscosity sufficient to stick to a bottom surface of the BCHD after having been disposed thereon by a user, the BCHD comprising a transducer configured to generate sound signals for transmission to a patient's skull, wherein the transducer is an electromagnetic ("EM") transducer, wherein the acoustically conductive gel or paste is configured for use in conjunction with the BCHD by being disposed over at least portions of the bottom surface and between the bottom surface and the patient's skull when the BCHD is secured, attached or magnetically coupled to the patient's head or skull, and the acoustically conductive gel or paste is further configured to improve acoustic coupling and transmission of the audible frequency components of sound signals originating from the transducer to the patient's skull, wherein the acoustically conductive gel or paste is water soluble, wherein the sound velocity of the acoustically conductive gel or paste ranges between 1,450 meters/second and 1,700 meters/second, and wherein the acoustically conductive gel or paste has a pH between 5.5 and 6.5.

33. The acoustically conductive gel or paste of claim 32, wherein the acoustically, conductive gel or paste comprises at least one of one or more of a cross-linked polyacrylate polymer, polyalkenyl ether, divinyl glycol propylene, glycol, glycerin, a carbomer, a carbopol, theolarnine, aloe vera, carrageenan, EDTA (Ethylenediaminetetraacetic acid), salt, vitamin E, a preservative, a thickening agent, and a neutralizer.

34. The acoustically conductive gel or paste of claim 32, wherein the acoustically conductive gel or paste is at least one of colorless, non-sterile, bacteriostatic, non-sensitizing to human skin, non-irritating to human skin, biocompatible, orally compatible, and ingestible.

35. The acoustically conductive gel or paste of claim 32, wherein the viscosity of the acoustically conductive gel or paste ranges between 10 Pascal-seconds and 20 Pascal-seconds.

36. The acoustically conductive gel or paste of claim 32, wherein the viscosity of the acoustically conductive gel or paste is sufficient to remain attached to the baseplate or spacer when applied thereon in a layer having a thickness ranging between 1 mm and 2 mm.

37. The acoustically conductive gel or paste of claim 32, wherein the acoustically conductive gel or paste has an acoustic impedance similar to soft human body tissue.

* * * * *